US007750181B2

(12) United States Patent
Ayuko et al.

(10) Patent No.: US 7,750,181 B2
(45) Date of Patent: Jul. 6, 2010

(54) ANTIPROLIFERATIVE AGENTS

(75) Inventors: Washington Odur Ayuko, Birmingham (GB); Michael John Tisdale, Claverdon (GB); Eric Lattmann, Birmingham (GB)

(73) Assignee: EPX Research Limited, Hampshire (GB)

( * ) Notice: Subject to any disclaimer, the term of this patent is extended or adjusted under 35 U.S.C. 154(b) by 1085 days.

(21) Appl. No.: 11/076,006

(22) Filed: Mar. 9, 2005

(65) Prior Publication Data

US 2005/0165066 A1 Jul. 28, 2005

Related U.S. Application Data

(60) Division of application No. 10/662,555, filed on Sep. 15, 2003, now Pat. No. 6,881,846, which is a continuation of application No. PCT/GB02/01119, filed on Mar. 12, 2002.

(51) Int. Cl.
*C07C 229/00* (2006.01)
*C07C 63/34* (2006.01)

(52) U.S. Cl. ............... 562/443; 562/450; 562/567; 564/161; 564/177; 564/192; 564/215

(58) Field of Classification Search ........... 564/177, 564/192, 215, 161; 562/443, 450, 567
See application file for complete search history.

(56) References Cited

FOREIGN PATENT DOCUMENTS

| EP | 0403240 A1 | 12/1990 | ............ 207/444 |
|----|------------|---------|---------------------|
| JP | 48 090982 A | 11/1973 | |
| JP | 0125034 | 5/1989 | ............ 207/448 |
| JP | 06100513 | 12/1994 | ............... 233/9 |

OTHER PUBLICATIONS

McGraw—Hill Dictionary of Chemical Terms(1990) pp. 282.*
Concise Encyclopedia Chemistry (1993), pp. 490.*
Hawlev's Condensed Chemical Dictionary (1993), pp. 594.*
Smolnk et al DN 67:64286 abstract (best available).*
Kume et al DN 121:133548 abstract (best available).*
Tsumura et al DN 115:49389 abstract (best available).*
Ibrahim et al DN 141:12547 abstract (best available).*
Romdhane et al.; "A Model study for Diels—Alder reaction of biscyclopentadienyl monomer with bismaleimides. Benzylcyclopentadiene: synthesis, Characterization and Diels—Alder reaction with N-(4-benzoyl)- phenylmaleimide." *Polymer 41*, 1633-1639 (2000).
Andreozzi, et al.; "Reactivity Towards Ozone of 2-Hydroxypyridine in Aqueous Solution." *Ozone Science & Engineering 14*, 177-184 (1992).
Smolanka et al.; "Some data on antimicrobial activity of the 4(5)-oxazolone and 4(5)-thiazolone derivatives" *Fiziol. AKT. Veshchestva 31-5* (1966).
Kaleagasiglu et al.; "Antiproliferative Activity of Retinoic Acid and Some Novel Retinoid Derivatives in Breast and Colorectal Cancer Cell Lines of Human Origin[1]." *Arzneim-Forsch/Drug Res 43 (I), Nr, 4* (1993).
Hixson et al.; "Antiproliferative Effect of Nonsteroidal Antiinflammatory Drugs against Human Colon Cancer Cells [1]." *Cancer Epidemiology, Blomarkers & Prenvention 3*, 433-438 (1994).
Rao et al.; "Electrochemical Studies of Some Amide Derivatives." *Transactions of the SAEST 32*, 2-3 (1997).

* cited by examiner

*Primary Examiner*—Janet L. Andres
*Assistant Examiner*—Raymond Covington
(74) *Attorney, Agent, or Firm*—Heslin Rothenberg Farley & Mesiti P.C.

(57) ABSTRACT

This invention relates to certain dioxodihydropyridine derivatives and certain methacrylic acid and furan derivative precursors thereof, processes for their preparation, pharmaceutical compositions containing such compounds and their use as anti-proliferative agents, especially tumour growth inhibitors and anti-cancer agents, antibiotics and/or antiviral agents.

10 Claims, No Drawings

ANTIPROLIFERATIVE AGENTS

CROSS-REFERENCE TO RELATED APPLICATIONS

This application is a divisional of U.S. Ser. No. 10/662,555 filed Sep. 15, 2003, now issued as U.S. Pat. No. 6,881,846, which is a continuation of PCT GB02/01119, filed Mar. 12, 2002, and published in English on Sep. 19, 2002 as WO 02/072553. PCT/GB02/01119 claimed the priority of British application 0106137.3, filed Mar. 13, 2001. The disclosures of both are incorporated herein by reference.

FIELD OF THE INVENTION

This invention relates to certain dioxodihydropyridine derivatives and certain methacrylic acid and furan derivative precursors thereof, processes for their preparation, pharmaceutical compositions containing such compounds and their use as anti-proliferative agents, especially tumour growth inhibitors and anti-cancer agents, antibiotics and/or antiviral agents.

BACKGROUND OF THE INVENTION

Various anti-cancer agents are known which are currently in clinical use. Some of these, such as cyclophosphamide and chlorambucil, are derived from the highly toxic group of N-Lost derivatives which contain a so-called N-Lost group, that is, a bis(2-chloroethyl)amino group. The original N-Lost derivatives are known to have cancer-triggering properties and were formerly used as chemical weapons. However, clinically acceptable compounds, such as cyclophosphamide and chlorambucil, have been prepared by modifying the original N-Lost structure to produce analogues with a significantly reduced toxicity. Nevertheless, these analogues all contain chemically reactive chlorine which is believed to be essential for their biological activity. In contrast, N-methylformamide is known as an anti-cancer agent but contains no chemically reactive chlorine.

SUMMARY AND DETAILED DESCRIPTION OF THE INVENTION

The present invention utilises the N-methylformamide moiety, sometimes in conjunction with the feature of chemically reactive halogen, especially chlorine, to produce biologically active compounds which are structurally distinct from the compounds discussed above. According to the present invention there is therefore provided a compound of the general formula

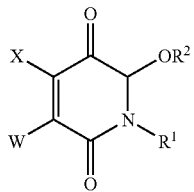

(I)

in which $R^1$ represents a hydrogen atom or an optionally substituted alkyl, alkenyl, alkynyl, cycloalkyl, cycloalkenyl, aryl, aralkyl, heterocyclyl or heterocyclylalkyl group; $R^2$ represents a hydrogen atom or an optionally substituted alkyl, alkenyl, alkynyl, cycloalkyl, cycloalkenyl, aryl, aralkyl, acyl, heterocyclyl or heterocyclylalkyl group; and W and X each independently represents a hydrogen or halogen atom.

Any alkyl, alkenyl or alkynyl group, unless otherwise specified, may be linear or branched and may contain up to 12, preferably up to 6, and especially up to 4 carbon atoms. Preferred alkyl groups are methyl, ethyl, propyl and butyl. Preferred alkenyl and alkynyl groups include propenyl, butenyl, propynyl and butynyl groups. When an alkyl moiety forms part of another group, for example the alkyl moiety of an aralkyl group, it is preferred that it contains up to 6, especially up to 4, carbon atoms. Preferred alkyl moieties are methyl and ethyl.

An aryl group may be any aromatic hydrocarbon group and may contain from 6 to 24, preferably 6 to 18, more preferably 6 to 16, particularly 6 to 14, and especially 6 to 10 carbon atoms. Preferred aryl groups include phenyl, naphthyl, anthryl, phenanthryl and pyryl groups, especially a phenyl or naphthyl, and particularly a phenyl, group. When an aryl moiety forms part of another group, for example the aryl moiety of an aralkyl group, it is preferred that it is a phenyl, naphthyl, anthryl, phenanthryl or pyryl, especially phenyl or naphthyl, and particularly a phenyl, moiety.

An aralkyl group may be any alkyl group substituted by an aryl group. A preferred aralkyl group contains from 7 to 30, particularly 7 to 24 and especially 7 to 18, carbon atoms, particularly preferred aralkyl groups being benzyl, naphthylmethyl, anthrylmethyl, phenanthrylmethyl and pyrylmethyl groups. A particularly preferred aralkyl group is a benzyl group.

A cycloalkyl group may be any saturated cyclic hydrocarbon group and may contain from 3 to 12, preferably 3 to 6, and especially 3 to 6, carbon atoms. Preferred cycloalkyl groups are cyclopropyl, cyclopentyl and cyclohexyl groups.

A cycloalkenyl group may be any cyclic hydrocarbon group which contains at least one carbon-carbon double bond. Thus, a cycloalkenyl group is effectively a cycloalkyl group in which at least one carbon-carbon single bond has been replaced by a carbon-carbon double bond. A cycloalkenyl group may therefore contain from 3 to 12, preferably 3 to 8, and especially 3 to 6, carbon atoms. Preferred cycloalkenyl groups are cyclopentenyl and cyclohexenyl groups.

An acyl group may be any group of the general formula R—CO— where R represents an optionally substituted alkyl, alkenyl, alkynyl, cycloalkyl, cycloalkenyl, aryl, aralkyl, heterocyclyl or heterocyclylalkyl group. Preferred acyl groups are alkanoyl, especially $C_{1-4}$ alkanoyl, and aroyl, especially benzoyl, groups.

A heteroaryl group may be any aromatic monocyclic or polycyclic ring system which contains at least one heteroatom. Preferably, a heteroaryl group is a 5- to 18-membered, particularly a 5- to 14-membered, and especially a 5- to 10-membered, aromatic ring system containing at least one heteroatom selected from oxygen, sulphur and nitrogen atoms. Preferred heteroaryl groups include pyridyl, pyrylium, thiopyrylium, pyrrolyl, furyl, thienyl, indolinyl, isoindolinyl, indolizinyl, imidazolyl, pyridonyl, pyronyl, pyrimidinyl, pyrazinyl, oxazolyl, thiazolyl, purinyl, quinolinyl, isoquinolinyl, quinoxalinyl, pyridazinyl, benzofuranyl, benzoxazolyl and acridinyl groups.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. Preferably, a heterocyclic group is a 3- to 18-membered, particularly a 3- to 14-membered, especially a 5- to 10-membered, ring system containing at least one heteroatom selected from oxygen, sulphur and nitrogen atoms. Preferred heterocyclic groups include the specific heteroaryl groups named above as well as pyranyl, piperidinyl, pyrrolidinyl, dioxanyl, piperazinyl, morpholinyl, thiomorpholinyl, morpholinosulphonyl, tetrahydroisoquinolinyl and tetrahydrofuranyl groups.

A heterocyclylalkyl group may be any alkyl group substituted by a heterocyclic group. Preferably, the heterocyclic moiety is a 3- to 18-membered, particularly a 3- to 14-membered, and especially a 5- to 10-membered, heterocyclic group as defined above and the alkyl moiety is a $C_{1-6}$ alkyl, preferably $C_{1-4}$ alkyl, and especially methyl, group.

When any of the foregoing substituents are designated as being optionally substituted, the substituent groups which are optionally present may be any one or more of those customarily employed in the development of pharmaceutical compounds and/or the modification of such compounds to influence their structure/activity, stability, bioavailability or other property. Specific examples of such substituents include, for example, halogen atoms, nitro, cyano, hydroxyl, cycloalkyl, alkyl, alkenyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, alkylsulphonato, arylsulphinyl, arylsulphonyl, arylsulphonato, carbamoyl, alkylamido, aryl and aralkyl groups.

When any of the foregoing optional substituents represents or contains an alkyl or alkenyl substituent group, this may be linear or branched and may contain up to 12, preferably up to 6, and especially up to 4, carbon atoms. A cycloalkyl group may contain from 3 to 8, preferably from 3 to 6, carbon atoms. An aryl group or moiety may contain from 6 to 10 carbon atoms, phenyl groups being especially preferred. A halogen atom may be a fluorine, chlorine, bromine or iodine atom and any group which contains a halo moiety, such as a haloalkyl group, may thus contain any one or more of these halogen atoms.

Preferred optional substituents include halogen atoms, nitro, cyano, hydroxyl, $C_{1-6}$ alkyl, $C_{1-6}$ haloalkyl, $C_{1-6}$ alkoxy, $C_{1-6}$ haloalkoxy, amino, $C_{1-6}$ alkylamino, di-($C_{1-6}$ alkyl) amino, formyl, $C_{1-6}$ alkoxycarbonyl, carboxyl, $C_{1-6}$ alkanoyl, $C_{1-6}$ alkylthio, $C_{1-6}$ alkylsulphinyl, $C_{1-6}$ alkylsulphonyl, carbamoyl and $C_{1-6}$ alkylamido groups. Particularly preferred optional substituents include halogen atoms, nitro, cyano, hydroxyl, $C_{1-4}$ alkyl, $C_{1-4}$ haloalkyl, $C_{1-4}$ alkoxy and $C_{1-4}$ haloalkoxy groups with halogen atoms being especially preferred.

Preferably, $R^1$ represents a $C_{1-12}$ alkyl or $C_{6-14}$ aryl group, each group being optionally substituted by one or more substituents selected from the group consisting of halogen atoms, nitro, cyano, hydroxyl, $C_{1-4}$ alkyl, $C_{1-4}$ haloalkyl, $C_{1-4}$ alkoxy and $C_{1-4}$ haloalkoxy groups. More preferably, $R^1$ represents a $C_{1-6}$ alkyl, especially a $C_{1-4}$ alkyl, group optionally substituted by one or more substituents selected from the group consisting of halogen atoms, nitro, cyano, hydroxyl, $C_{1-4}$ alkoxy and $C_{1-4}$ haloalkoxy groups. It is particularly preferred that $R^1$ represents an unsubstituted $C_{1-4}$ alkyl group, especially a methyl group.

It is preferred that $R^2$ represents a hydrogen atom or a $C_{1-12}$ alkyl or $C_{6-14}$ aryl group, each group being optionally substituted by one or more substituents selected from the group consisting of halogen atoms, nitro, cyano, hydroxyl, $C_{1-4}$ alkyl, $C_{1-4}$ haloalkyl, $C_{1-4}$ alkoxy and $C_{1-4}$ haloalkoxy groups. More preferably, $R^2$ represents a hydrogen atom or a $C_{1-6}$ alkyl, especially a $C_{1-4}$ alkyl, group optionally substituted by one or more substituents selected from the group consisting of halogen atoms, nitro, cyano, hydroxyl, $C_{1-4}$ alkoxy and $C_{1-4}$ haloalkoxy groups. It is particularly preferred that $R^2$ represents a hydrogen atom or an unsubstituted $C_{1-4}$ alkyl, especially a methyl group. Most preferably, $R^2$ represents a hydrogen atom.

Preferably, W and X each independently represents a hydrogen, chlorine or bromine atom, especially a hydrogen or chlorine atom. More preferably, W and X are both the same.

In a particularly, preferred sub-group of compounds of formula I, $R^1$ represents a methyl group, $R^2$ represents a hydrogen atom and W and X both represent a hydrogen atom or both represent a chlorine atom.

It should be appreciated that compounds of general formula I in which $R^2$ represents a hydrogen atom can tautomerise. The three main tautomeric forms are set out below:

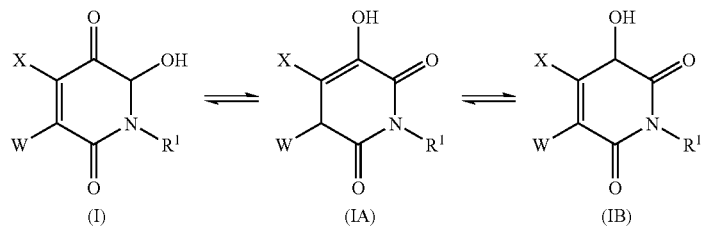

The present invention thus includes both the individual tautomers and mixtures of such tautomers.

Particularly preferred compounds include 3,4-dichloro-6-hydroxy-1-methyl-2,5-dioxo-1,6-dihydropyridine (also known as 3,4-dichloro-6-hydroxy-1-methyl-1,6-dihydropyridine-2,5-dione) and 6-hydroxy-1-methyl-2,5-dioxo-1,6-dihydropyridine (also known as 6-hydroxy-1-methyl-1,6-dihydropyridine-2,5-dione), with the former compound being especially preferred.

The invention also provides a process for the preparation of a compound of the general formula I as defined above which comprises reacting a compound of the general formula

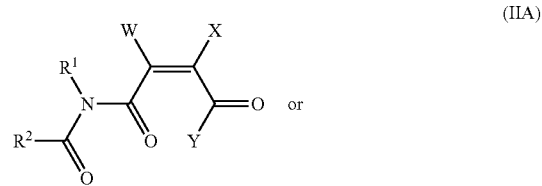

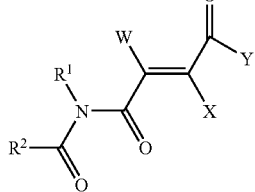

(IIB)

in which $R^1$, $R^2$, W and X are as defined above and Y represents a hydrogen atom, a hydroxyl group or a group —OM where M represents an alkali metal atom, with a base in the presence of a compound of the general formula

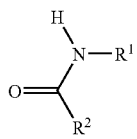

(III)

in which $R^1$ and $R^2$ are as defined above.

It is preferred that Y represents a hydrogen atom, a hydroxyl group or a group —OM where M represents a sodium or potassium atom. More preferably, Y represents a hydroxyl group.

The base may be an organic or inorganic base. Suitable organic bases include pyridine and tertiary amines, such as triethylamine. Suitable inorganic bases include carbonates and hydrogencarbonates of alkali metals and alkaline earth metals, such as sodium, potassium, lithium, calcium, magnesium, etc. In general, inorganic bases are preferred with sodium hydrogencarbonate being especially preferred.

Preferably, the reaction is carried out in the presence of an acyl halide. Suitable acyl halides include $C_{2-4}$ acyl halides and halo $C_{2-4}$ acyl halides, with acetyl chloride and dichloroacetyl chloride being especially preferred.

The reaction is preferably carried out at a temperature from 0 to 80° C., with 60° C. being particularly preferred.

A possible reaction scheme for this process is set out in Scheme I below:—

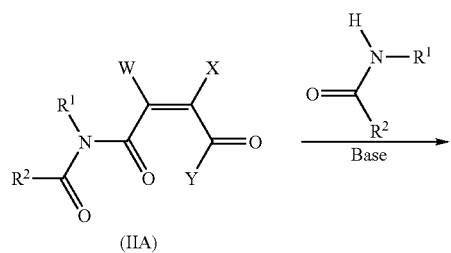

(IIA)

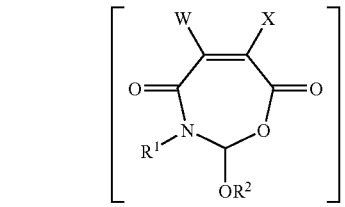

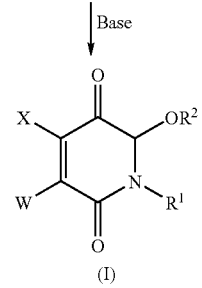

(I)

On the basis of the above proposed reaction scheme, it may be necessary or desirable to convert any compound of formula IIB to the corresponding compound of formula IIA to facilitate the reaction. This can be readily achieved by exposure to ultra violet light. Thus, exposure to ultra violet light is an optional additional step in the process of the invention.

The invention also provides a process for the preparation of a compound of the general formula IIA or IIB as defined above which comprises reacting a compound of the general formula

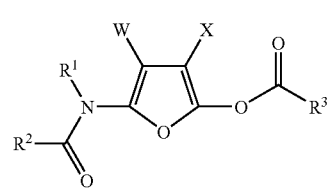

(IV)

in which $R^1$, $R^2$, W and X are as defined above and $R^3$ represents an optionally substituted alkyl, aryl or aralkyl group, with a base.

This process produces a mixture of compounds of formula IIA and IIB. Under normal conditions, this process will produce a mixture containing about 80% compounds of formula IIA and about 20% compounds of formula IIB. However, the quantity of compounds of formula IIB can be increased by using more heat in the process and the quantity of compounds of formula IIA can be increased by exposure to ultra violet light.

Preferably, $R^3$ represents a $C_{1-6}$ alkyl, especially a $C_{1-4}$ alkyl, group optionally substituted by one or more substituents selected from halogen atoms, nitro, cyano, hydroxyl, $C_{1-4}$ alkoxy and $C_{1-4}$ haloalkoxy groups, with halogen atoms, especially chlorine atoms, being particularly preferred as optional substituents. More preferably, $R^3$ represents a $C_{1-4}$ alkyl group optionally substituted by one or more halogen, especially chlorine, atoms. It is especially preferred that $R^3$ represents a chloromethyl or dichloromethyl group The base may be an organic or inorganic base. Suitable organic bases include pyridine and tertiary amines, such as triethylamine. Suitable inorganic bases include carbonates and hydrogencarbonates of alkali metals and alkaline earth metals, such as sodium, potassium, lithium, calcium, magnesium, etc. In general, inorganic bases are preferred with sodium hydrogencarbonate being especially preferred.

The reaction is preferably carried out at a temperature of 0 to 80° C., with 60° C. being particularly preferred.

According to another aspect of the invention, compounds of formula IV as defined above can be prepared by reacting a compound of the general formula

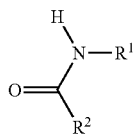

(III)

in which $R^1$ and $R^2$ are as defined above, with a compound of the general formula

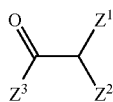

(V)

in which $Z^1$ and $Z^2$ each independently represents a hydrogen or halogen, especially a chlorine, atom and $Z^3$ is a halogen, preferably a chlorine, atom.

Preferably, the compound of general formula III is reacted with an excess of the compound of general formula V. More preferably, the molar ratio of the compound of general formula V to the compound of general formula III is at least 2:1. Thus, at least two equivalents of the compound of general formula V are used for each equivalent of the compounds of the general formula III.

Preferably, the reaction is carried out at a temperature of from 0° C. to the reflux temperature of the reaction mixture, especially at 60° C. to the reflux temperature of the reaction mixture. In general, an increase in reaction temperature results in an increase in the yield of the desired product of general formula IV.

Compounds of the general formula III and V are known compounds or can be prepared from known compounds by processes analogous to known processes.

A reaction scheme for this process is set out in Scheme II below:—

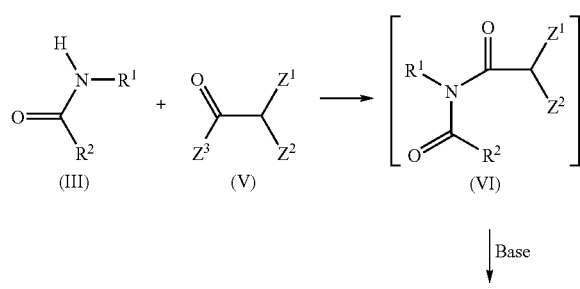

-continued

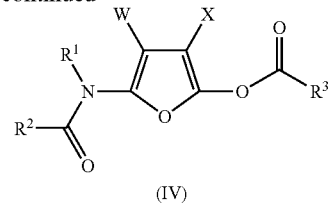

(IV)

This process provides a general method for synthesising 2,5-substituted furan derivatives in a one-pot reaction. However, if desired, the amide intermediate of the general formula V can be isolated.

The processes set out above describe the preparation of compounds of the general formulae I, IIA, IIB and IV in separate steps. However, compounds of formula I can be prepared in a one-pot reaction starting from compounds of formulae III and V and this may be particularly advantageous.

The compounds of general formula IIA and IIB are novel. According to another aspect of the invention there is therefore provided a compound of the general formula

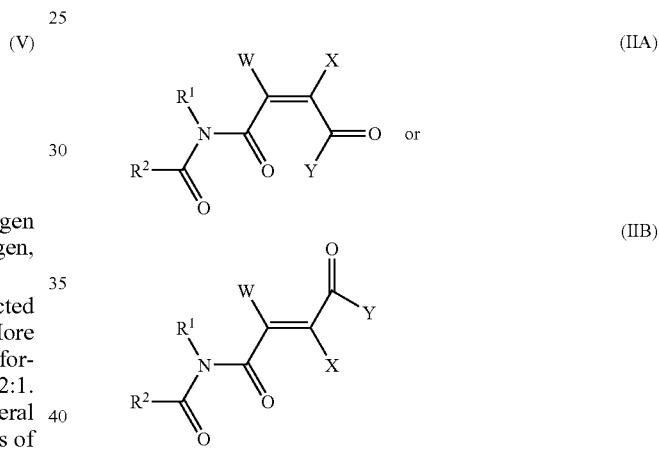

or a salt thereof, in which $R^1$, $R^2$, W, X and Y are as defined above.

Suitable salts include acid addition salts and these may be formed by reaction of a suitable compound of formula IIA or IIB with a suitable acid, such as an organic acid or a mineral acid. Acid addition salts formed by reaction with a mineral acid are particularly preferred, especially salts formed by reaction with hydrochloric or hydrobromic acid.

It should be appreciated that the compounds of general formula IIA and IIB are geometric isomers of each other. The present invention thus includes both the individual isomers and mixtures of such isomers.

Particularly preferred compounds include (E)- and (Z)-2, 3-dichloro-4-[N-formyl-N-methylamino]-4-oxo-but-2-enoic acid (also known as (E)- and (Z)-4-(N-methylformamido)-4-oxo-2,3-dichloromethacrylic acid) and (E)- and (Z)-4-[N-formyl-N-methylamino]-4-oxo-but-2-enoic acid (also known as (E)- and (Z)-4-(N-methylformamido)-4-oxo-methacrylic acid), with the former compounds being especially preferred. The Z-isomers of these compounds are particularly preferred.

The compounds of general formula IV are also novel and the invention therefore further provides a compound of the general formula

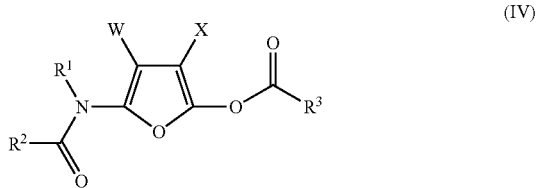

in which $R^1$, $R^2$, $R^3$, W and X are as defined above. Preferred compounds of formula IV include 5-[N-formyl-N-methylamino]-3,4-dichloro-2-furyl-2,2-dichloroacetate (also known as 3,4-dichloro-2-(N-methylformamido)-5-dichloroacetoxyfuran) and 5-[N-formyl-N-methylamino]-2-furyl-2-chloroacetate (also known as 2-(N-methylformamido)-5-chloroacetoxyfuran), with the former compound being especially preferred.

The compounds of general formulae I, IIA and IIB have been found to be effective in the treatment and/or prophylaxis of a variety of diseases, particularly disorders involving cell proliferation, such as cancer, cancer metastasis and the growth of non-malignant tumours, as well as diseases caused by bacteria or other microbes and viral diseases. These compounds exhibit a wide spectrum of anti-cancer activity. However, they are particularly suitable for the treatment of lung, ovary and/or colon cancer. Moreover, since the compounds of general formula IV can be readily converted into compounds of general formula IIA or IIB in the presence of a base, the compounds of general formula IV function as prodrugs. The term "prodrug" refers to a compound whose metabolite possesses therapeutic utility greater than the compound itself. The metabolite arises from chemical and/or enzymatic transformations in vivo following administration of the prodrug.

In view of the above, the present invention also provides a compound of the general formula I as defined above and/or a compound of the general formula IIA or IIB or a salt thereof as defined above and/or a compound of the general formula IV as defined above for use in medicine, particularly as an anti-proliferative agent, an antibiotic or an anti-viral agent, and especially as a tumour growth inhibitor and/or anti-cancer agent.

The invention also includes the use of a compound of the general formula I as defined above and/or a compound of the general formula IIA or IIB or a salt thereof as defined above and/or a compound of the general formula IV as defined above for the manufacture of a medicament for use as an anti-proliferative agent, an antibiotic or an anti-viral agent, and especially as a tumour growth inhibitor and/or anti-cancer agent.

In another aspect, the invention provides a method for treating or preventing a disorder involving cell proliferation, a disease caused by a bacterium or a microbe or a viral disease which comprises administering to a patient a therapeutically or prophylactically effective amount of a compound of the general formula I as defined above and/or a compound of the general formula IIA or IIB or a salt thereof as defined above and/or a compound of the general formula IV as defined above. Preferably, the disorder involving cell proliferation is cancer, cancer metastasis or the growth of a non-malignant tumour.

In a further aspect, the invention provides a compound of the general formula IV as defined above for use as a prodrug. The use of a compound of the general formula IV as defined above for the manufacture of a medicament for use as a prodrug is also provided.

The invention also provides a pharmaceutical composition which comprises a carrier and, as active ingredient, a compound of the general formula I as defined above and/or a compound of the general formula IIA or IIB or a salt thereof as defined above and/or a compound of the general formula IV as defined above. A process for the preparation of a pharmaceutical composition as defined above is also provided which comprises bringing a compound of the general formula I as defined above and/or a compound of the general formula IIA or IIB or a salt thereof as defined above and/or a compound of the general formula IV as defined above into association with a carrier.

A pharmaceutically acceptable carrier may be any material with which the active ingredient is formulated to facilitate administration. A carrier may be a solid or a liquid, including a material which is normally gaseous but which has been compressed to form a liquid, and any of the carriers normally used in formulating pharmaceutical compositions may be used. Preferably, compositions according to the invention contain 0.5 to 95% by weight of active ingredient.

The compounds of general formula I, general formula IIA and IIB and general formula IV can be formulated as, for example, tablets, capsules, suppositories or solutions. These formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include sodium hydrogencarbonate, citric acid, tartaric acid, phosphoric acid, hydrochloric acid and maleic acid. Suitable sweeteners include aspartame, acesulfame K and thaumatin. Suitable taste-masking agents include sodium hydrogencarbonate, ion-exchange resins, cyclodextrin inclusion compounds, adsorbates or microencapsulated actives.

The inclusion of a compound which is capable of generating an alkaline environment in the body or the co-administration of a base may be particularly advantageous when the composition contains a compound of formula IV to encourage the conversion of such a compound into a compound of formula IIA or IIB.

For treatment of and prophylaxis against disorders involving cell proliferation, diseases caused by bacteria or microbes or viral diseases, amounts of 0.5 to 100, preferably 20 to 50, mg/kg body weight active compound are preferably administered daily to obtain the desired results. Nevertheless, it may be necessary from time to time to depart from the amounts mentioned above, depending on the body weight of the patient, the method of application, the animal species of the patient and its individual reaction to the drug or the kind of formulation or the time or interval in which the drug is applied. In special cases, it may be sufficient to use less than the minimum amount given above, whilst in other cases the maximum dose may have to be exceeded. For a larger dose, it may be advisable to divide the dose into several smaller single doses.

The invention is further illustrated by the following examples.

EXAMPLE 1

Preparation of N-methyl-N-formyl-α,α-dichloroacetamide (Formula VI: $R^1$=—$CH_3$; $R^2$=—H; Z=Cl)

25 g of dichloroacetyl chloride (1.25 eq.) was added to a solution of 50 g N-methylformamide (NMF) in chloroform at ambient temperature. The reaction mixture was washed with an aqueous solution of sodium hydrogencarbonate, dried with magnesium sulfate and the solvent was evaporated off in vacuum to give N-methyl-N-formyl-α,α-dichloroacetamide (86% yield) in high purity as a yellow oil. The chemical structure was confirmed by APCl-MS, FT-IR, 1H and 13C magnetic resonance spectroscopy.

$^1$H-NMR (DMSO-$d_6$): 3.11 (d, 3H, $NCH_3$, J=4.7 Hz); 6.58+5.93 (s, 1H, $COCHCl_2$); 9.19 (br.s., 1H, NCOH); $^{13}$C-NMR (DMSO-$d_6$): 25.36+26.78; 64.23+64.83; 162.95, 165.44+166.32; IR (KBr): 3394, 1702, 1667, 1162, 670; MS (APCl+, m/z): 171 ($M^+$+1).

N-methyl-α,α-dichloroacetamide precipitated out within a couple of days in a freezer as white needles (48% yield). The chemical structure was confirmed by APCl-MS, FT-IR, 1H and 13C magnetic resonance spectroscopy.

$^1$H-NMR (DMSO-$d_6$): 2.67 (d, 3H, $NCH_3$, J=4.7 Hz.); 6.44 (s, 1H, $COCHCl_2$); 8.51 (br.s., 1H, NH); $^{13}$C-NMR (DMSO-$d_6$): 26.78, 67.32, 164.53; IR (KBr): 3394, 1666, 1162, 670; MS (APCl+, m/z): 143 ($M^+$+1).

EXAMPLE 2

Preparation of 5-[N-formyl-N-methylamino]-3,4-dichloro-2-furyl-2,2-dichloroacetate (also known as 3,4-dichloro-2-(N-methylformamido)-5-dichloroacetoxyfuran) (One-pot synthesis)

(Formula IV: $R^1$=—$CH_3$; $R^2$=—H; $R^3$=—$CHCl_2$; W=X=Cl.)

60 ml of NMF were added in portions to 140 ml of dichloroacetyl chloride. After the first addition of NMF, the temperature was increased and the addition of NMF was continued in portions, so that the mixture proceeded to reflux gently. The reaction was completed after several hours. For workup, the reaction mixture was poured onto ice and the remaining oily residue was washed repeatedly with water. The oil was dissolved in dichloromethane (DCM) and the solution of the furan in DCM was washed many times with water. The organic phase was dried with magnesium sulfate and the solvent was carefully removed at room temperature in vacuum. The title compound was obtained as pure, yellow-orange oil (72% yield). The chemical structure of the furan was confirmed by APCl-MS, FT-IR, 1H and 13C magnetic resonance spectroscopy.

$^1$H-NMR (CDCl$_3$-$d_6$): 9.28 (s, 1H, CHO), 6.52 (s, 1H, ClClH), 3.19 (s, 3H, N-Me);
$^{13}$C-NMR (CDCl$_3$-$d_6$): 165.55, 165.19+162.12 (CHO), 165.09, 165.03 (COClCl), 157.86, 140.12, 66.10+53.60 (C—ClCl), 28.45+28.07 (N-Me: MS (ACPI+, m/z): 342, 341, 340 [($M^+$+1)+OH], 324, 323, 322 (M+1), 212, 210 [(M+1)-OAc], 183, 182 (210-CO)

EXAMPLE 3

Preparation of (Z)-2,3-dichloro-4-[N-formyl-N-methylamino]-4-oxo-but-2-enoic acid (also known as (Z)-4-(N-methylformamido)-4-oxo-2,3-dichloromethacrylic acid)

(Formula IIA: $R^1$=—$CH_3$; $R^2$=—H; W=X=Cl; Y=—OH)

2 g of 5-[formyl(methyl)amino]-3,4-dichloro-2,2-dichloroacetate prepared as described in Example 2 were mixed with 1.5 g of solid sodium hydrogencarbonate and 5 ml of water. The mixture was shaken vigorously under development of carbon dioxide. After 3 hours a homogeneous solution of the title compound in water was obtained and the sodium dichloroacetate which precipitated out was filtered off. Water was added to this solution until a total volume of 10 ml was obtained. This solution was then used to evaluate the efficacy of this compound in animal tumour models (see Example 4 below).

Content: 10%

10 mg in 100 µl

The title compound was independently isolated as a non-distillable viscous, water-soluble liquid. The chemical structure was confirmed by APCl-MS, FT-IR, 1H and 13C magnetic resonance spectroscopy.

$^1$H-NMR (D$_2$O), MeOD-$d_6$): 7.77 (s, 1H, CHO), 2.53 (s, 3H, Me) $^{13}$; C-NMR (D$_2$O, MeOD-$d_6$): 169.13, 166.32, 165.14, 163.04, 162.95, 24.33 (Me); MS (APCl+, m/z): 241, 239 (OMe), 229, 230 (OH), 210, 184 (—CO)

EXAMPLE 4

Preparation of 3,4-dichloro-6-hydroxy-1-methyl-2,5-dioxo-1.6-dihydropyridine (also known as 3,4-dichloro-6-hydroxy-1-methyl-1,6-dihydropyridine-2,5-dione) (One-pot synthesis) (Formula I: $R^1$=$CH_3$; $R^2$=H; W=X=Cl 60 ml NMF were added in portions to 140 ml of dichloroacetyl chloride. After the first addition of NMF, the temperature was increased and the addition of NMF was continued in portions, so that the mixture proceeded to reflux gently. The reaction was completed within a couple of hours.

Method A 20 g of the reaction mixture was mixed with 15 g solid sodium hydrogencarbonate and 50 ml of water. The reaction mixture was extracted with ether in a Ludwig (continuous extraction unit) extractor overnight. The ether solution was dried with magnesium sulphate and was evaporated off under reduced pressure. The remaining yellow oil was distilled in a fine vacuum to give the title compound in 40% yield.

Method B 15 g of solid sodium hydrogencarbonate was added to 20 g of the crude material. A small amount of water was added followed by ethyl acetate as solvent. If the reaction rate decreased, more water was added. After the reaction was completed, the solution was dried with magnesium sulphate and the solvent was distilled off. The distillation of the remaining oil gave the title compound in 35% yield.

$^1$H-NMR (DMSO-$d_6$): 7.6 (bs, 1H, OH); 6.0 (s, 1H)

$^{13}$C-NMR (DMSO-$d_6$): 25.36+26.78; 102.5 (C6); 123.44, 126.6 (C3, C4), 156, 162 (CO); IR (KBr): 3610, 3394, 1702, 1715, 1667, 1162, 670;

MS (APCl+, m/z): 210 (M$^+$+1)

EXAMPLE 5

Assessment of Tumour Growth Inhibition

Pure strain NMRI mice (age 6-8 weeks) from our inbred colony were used for transplanting MAC (murine colon cancer) tumours, M5076 reticulum cell sarcoma (ovarian) were transplanted in BDF1 mice purchased from Harlan, Bicester, U.K. Animals were fed on RM3E diet (Lillco-England) and water ad libitum.

MAC 13 and M5076

Approximately 2×2 mm of MAC13 tumour fragments were transplanted subcutaneously in the inguinal region via a trocar while the M5076 was homogenised and 1×10$^6$ cells transplanted intramuscularly in the inguinal region. Tumour bearing mice were randomised in groups of 5-7 animals per group. Treatment commenced one day after transplant for M5076 and two days for MAC13. Untreated or vehicle controls were included. Daily weights were recorded. Chemotherapy effects were assessed on day 14 or thereabouts depending on the tumour sizes and condition of the animals. Mice were killed and the effects of the chemotherapy were assessed by the differences in tumour weights and expressed as:

% T/C, i.e. inhibition=100-Treated weight/Control weight×100%

Body weight changes were recorded in order to assess toxicity.

MAC15A

The tumour is routinely passaged as an ascites. Approximately 2×10$^5$ cells were transplanted subcutaneously in saline in a volume of 0.2 ml. Mice were randomised in groups of 5-7 animals per group. Untreated or vehicle controls were included. Treatment commenced two days after transplant. Body weight was recorded daily. The effects of chemotherapy were assessed between 7-9 days after transplant. Mice were killed and the effects measured by the differences in tumour weights and expressed as:

% T/C, i.e. inhibition=Treated weight/Control weight×100%

Body weight changes were recorded in order to assess toxicity.

The results are set out in Tables 1, 2, 3 and 4 below

TABLE 1

The effect of the compound of Example 3 on the growth of MAC 13 tumour, murine colon cancer, transplanted s.c. on NMRI mice and treatment given by intraperitoneal route

| Dose: mg/kg body weight | Tumour weight (g) | Tumour weight (g) | Tumour weight (g) | Tumour weight (g) | Tumour weight (g) | Tumour weight (g) | Mean tumour weight | sem | % Tumour growth inhibition | Days of treatment |
|---|---|---|---|---|---|---|---|---|---|---|
| 400 | 0.053 | 0.045 | 0.030 | 0.023 | 0.0 | 0.036 | 0.031 | 0.007 | 92 | 1-5 |
| Control untreated | 0.413 | 0.304 | 0.270 | 0.538 | 0.641 | 0.209 | 0.395 | 0.068 | 0 | — |

TABLE 2

The effect of the compound of Example 3 on the growth of M5076 tumour, ovarian cancer transplanted i.m. on BDF1 mice and treatment by intraperitoneal route.

| Dose: mg/kg body weight | Tumour weight (g) | Tumour weight (g) | Tumour weight (g) | Tumour weight (g) | Tumour weight (g) | Tumour weight (g) | Mean tumour weight | sem | % Tumour growth inhibition | Days of treatment |
|---|---|---|---|---|---|---|---|---|---|---|
| 400 | 0 | 0 | 0 | 0 | 0 | 0.052 | 0.008 | 0.008 | 97 | 1-11 |
| Control untreated | 0.591 | 0.235 | 0.032 | 0.162 | 0.449 | 0.288 | 0.292 | 0.082 | 0 | |

TABLE 3

The effect of the compound of Example 3 on the growth of MAC15 tumour, murine colon cancer, transplanted s.c. on NMRI mice and treatment given by intraperitoneal route.

| Dose: mg/kg body weight | Tumour weight (g) | Tumour weight (g) | Tumour weight (g) | Tumour weight (g) | Tumour weight (g) | Tumour weight (g) | Mean tumour weight | sem | % Tumour growth inhibition | Days of treatment |
|---|---|---|---|---|---|---|---|---|---|---|
| 400 | 0.074 | 0.094 | 0.190 | 0.096 | 0.132 | — | 0.117 | 0.02 | 81 | 1-5 |
| 300 | 0.194 | 0.201 | 0.190 | 0.176 | 0.214 | — | 0.195 | 0.006 | 68 | 1-5 |

TABLE 3-continued

The effect of the compound of Example 3 on the growth of MAC15 tumour, murine colon cancer, transplanted s.c. on NMRI mice and treatment given by intraperitoneal route.

| Dose: mg/kg body weight | Tumour weight (g) | Tumour weight (g) | Tumour weight (g) | Tumour weight (g) | Tumour weight (g) | Tumour weight (g) | Mean tumour weight | sem | % Tumour growth inhibition | Days of treatment |
|---|---|---|---|---|---|---|---|---|---|---|
| Control untreated | 0.581 | 0.617 | 0.770 | 0.612 | 0.417 | — | 0.610 | 0.056 | 0 | — |

TABLE 4

The effect of the compound of Example 4 on the growth of MAC15 tumour, murine colon cancer, transplanted s.c. on NMRI mice and treatment given by intraperitoneal route from day 1-5.

| Dose: mg/kg body weight | Tumour weight (g) | Tumour weight (g) | Tumour weight (g) | Tumour weight (g) | Tumour weight (g) | Tumour weight (g) | Tumour weight (g) | Tumour weight (g) | Tumour weight (g) | Tumour weight (g) | Mean tumour weight | sem | % Tumour growth inhibition |
|---|---|---|---|---|---|---|---|---|---|---|---|---|---|
| 500 | 0.076 | 0.033 | 0.0 | 0.090 | 0.060 | 0.0 | 0.134 | 0.114 | 0.0 | — | 0.056 | 0.017 | 86 |
| Control untreated | 0.342 | 0.518 | 0.437 | 0.312 | 0.444 | 0.328 | 0.561 | 0.239 | 0.340 | 0.459 | 0.398 | 0.032 | 0 |

EXAMPLE 6

Antitumour Test Protocol and Results for H460 Non-Small Cell Lung (NSCLC) and DLD-1 Colon Cancers Human Xenograft Fragments of the non-small cell lung cancer, H460, and DLD-1 colon cancer human xenografts were transplanted sub-cutaneously in both flanks of 14 female Nu nude mice from an inbred colony (B7K Universal, Hull, UK). Mice received CRM diet (SDS, WItham, UK) and water ad libitum. All experiments were carried out under a project license issued by the UK Home Office, and UKCCCR guidelines were followed throughout.

Therapy commenced once tumours had grown to a sufficient size to be measured accurately (minimum 4 mm×4 mm), which was 10 days for H460 and 19 days for DLD-1. 10 tumours grew sufficiently to use in 7 mice for both the test and untreated groups.

In the case of H460, the compound of Example 4 was administered at a concentration of 500 mg/kg body weight/day, intraperitoneally (i.p.), daily for 5 days (designated days 0-4). Animals were monitored daily for any toxicity effects, and tumours were measured, and weights recorded daily over the period of therapy and then on day 7 (untreated and test groups), and day 8 (test group). On day 7 for the untreated group, and day 8 for the test group, the largest tumour diameter was greater than the maximum permitted 17 mm, and subjects were then euthenised by UK Home Office Schedule 1 methods.

Antitumour activity against DLD-1 was assessed by dosing i.p. daily for 5 days (500 mg/kg body weight/day) followed by a 2 day break, and then dosing for a further 5 days, and assessing tumour growth compared to a control untreated group until the tumours have reached the maximum permitted size (day 16 control and tested group).

In both cases tumour volumes were assessed by caliper measurements of 2 perpendicular diameters and the volumes estimated using the following equation:

Volumes=$(a^2 \times b)/2$, where a is the smaller, and b the larger diameter of the two. The effects of the therapy were determined from the difference in tumour volume-doubling time between treated and control groups, and the significance of any tumour growth delay determined using the Mann-Whitney U Test.

The results are set out in Tables 5 and 6 below.

1. H460 NSCLC xenograft

TABLE 5

| Group Number | Mean time to RTV2 (days) | Median time RTV2 (days) | Growth delay (days) | Significance | Maximum % weight loss |
|---|---|---|---|---|---|
| 1 | 2.6 | 2.5 | — | — | 4.9 |
| 2 | 6.2 | 6.4 | 3.9 | P < 0.01 | 6.9 |

GROUP 1 - untreated controls
GROUP 2 - Compound of Example 4, 500 mg/kg, i.p. days 0-4

2. DLD-1 colon cancer xenograft.

TABLE 6

| Group Number | Mean time to RTV2 (days) | Median time RTV2 (days) | Growth delay (days) | Significance | Maximum % weight loss |
|---|---|---|---|---|---|
| 1 | 3.2 | 3.1 | — | — | 3.2 |
| 2 | 9.9 | 9.8 | 6.7 | P < 0.01 | 4.3 |

GROUP 1 - untreated controls
GROUP 2 - Compound of Example 4, 500 mg/kg, i.p. days 0-4
RTV2 = Relative Tumour Volume Doubling.

The invention claimed is:

1. A compound of the general formula IIA or IIB

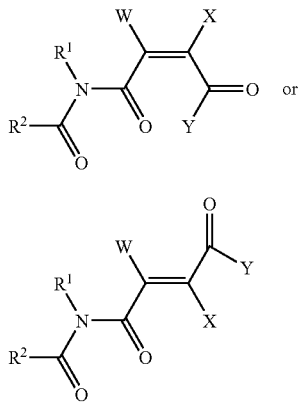

or a salt thereof, in which $R^1$ represents an optionally substituted alkyl, alkenyl, alkynyl, cycloalkyl, cycloalkenyl, aryl or aralkyl, group; $R^2$ represents a hydrogen atom or an optionally substituted alkyl, alkenyl, alkynyl, cycloalkyl, cycloalkenyl, aryl, aralkyl or acyl group; and W and X each independently represents a hydrogen or halogen atom and Y represents a hydrogen atom, a hydroxyl group or a group —OM where M represents an alkali metal atom.

2. A compound according to claim 1 in which Y represents a hydrogen atom, a hydroxyl group or a group —OM where M represents a sodium or potassium atom.

3. A compound according to claim 1 in which $R^1$ represents a methyl group, $R^2$ represents a hydrogen atom, W and X both represent a hydrogen atom or both represent a chlorine atom, and Y represents a hydroxyl group.

4. (Z)-2,3-dichloro-4-[N-formyl-N-methylamino]-4-oxo-but-2-enoic acid.

5. A process for the preparation of a compound according to claim 1, which comprises reacting with a base a compound of the general formula

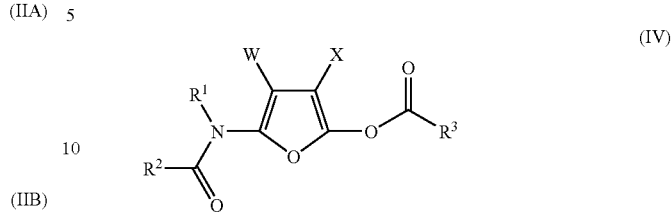

in which $R^1$, $R^2$, W and X are as defined in claim 8 and $R^3$ represents an optionally substituted alkyl, aryl or aralkyl group.

6. A pharmaceutical composition comprising a carrier and one or more compounds according to claim 1.

7. A method for inhibiting tumor growth comprising administering to a patient a therapeutically effective amount of a compound according to claim 1.

8. A compound according to claim 1 in which $R^1$ represents a $C_{1-12}$ alkyl or $C_{6-14}$ aryl group, each group being optionally substituted by one or more substituents selected from the group consisting of halogen atoms, nitro, cyano, hydroxyl, $C_{1-4}$ alkyl, $C_{1-4}$ haloalkyl, $C_{1-4}$ alkoxy and $C_{1-4}$ haloalkoxy groups.

9. A compound according to claim 1 in which $R^2$ represents a hydrogen atom or a C1-12 alkyl or C6-14 aryl group, each group being optionally substituted by one or more substituents selected from the group consisting of halogen atoms, nitro, cyano, hydroxyl, $C_{1-4}$ alkyl, $C_{1-4}$ haloalkyl, $C_{1-4}$ alkoxy and $C_{1-4}$ haloalkoxy groups.

10. A compound according to claim 1 in which W and X each independently represents a hydrogen, chlorine or bromine atom.

* * * * *